(12) United States Patent
Bourlon et al.

(10) Patent No.: US 10,247,690 B2
(45) Date of Patent: Apr. 2, 2019

(54) DEVICE FOR ANALYSIS OF MIXTURES OF AT LEAST TWO GASES

(71) Applicant: Commissariat A L'Energie Atomique et aux Energies Alternatives, Paris (FR)

(72) Inventors: Bertrand Bourlon, Saint Martin le Vinoux (FR); Bao-An Pham Ho, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 34 days.

(21) Appl. No.: 15/209,067

(22) Filed: Jul. 13, 2016

(65) Prior Publication Data

US 2017/0016840 A1   Jan. 19, 2017

(30) Foreign Application Priority Data

Jul. 16, 2015 (FR) ..................................... 15 56724

(51) Int. Cl.
  *G01N 27/18* (2006.01)
  *G01N 25/18* (2006.01)
  *G01N 33/00* (2006.01)

(52) U.S. Cl.
  CPC ............. *G01N 27/18* (2013.01); *G01N 25/18* (2013.01); *G01N 33/0004* (2013.01); *G01N 33/0031* (2013.01)

(58) Field of Classification Search
  USPC ............................................ 73/25.01, 25.03
  See application file for complete search history.

(56) References Cited

U.S. PATENT DOCUMENTS

| 4,164,862 A | 8/1979 | Jackson ..................... 73/5.03 |
| 2009/0100906 A1* | 4/2009 | Bonne ................... B82Y 15/00 |
| | | 73/25.03 |

(Continued)

FOREIGN PATENT DOCUMENTS

| DE | 10 2013 103 388 B3 | 9/2014 |
| FR | 2 995 691 A1 | 3/2014 |
| WO | WO 2011/044547 A2 | 4/2011 |

OTHER PUBLICATIONS

Extended European Search Report dated Sep. 16, 2016 in Patent Application No. 16179042.3.

(Continued)

*Primary Examiner* — Clayton E Laballe
*Assistant Examiner* — Warren K Fenwick
(74) *Attorney, Agent, or Firm* — Oblon, McClelland, Maier & Neustadt, L.L.P.

(57) ABSTRACT

Device for analyzing a mixture of n gases, comprising a microfluidic channel (2) extending between a first end and a second end, at least n−1 suspended elements in the microfluidic channel (2), said n−1 elements (S1, S2 . . . Sn−1) succeeding one another from the first end of the microfluidic channel (2) to the second end of the microfluidic channel (2), heating means capable of heating a part at least of the gaseous mixture surrounding each suspended element (S1, S2 . . . Sn−1) to a given temperature different to those to which are heated the gaseous mixtures surrounding the other suspended elements (S1, S2 . . . Sn−1), means of measuring the temperature or the variation in temperature of the suspended elements (S1, S2 . . . Sn−1) and a control and measurement system (UC) connected to the heating means and to the measuring means.

22 Claims, 6 Drawing Sheets

(56) References Cited

U.S. PATENT DOCUMENTS

| | | | |
|---|---|---|---|
| 2012/0024043 A1 | 2/2012 | Mcbrady et al. | 73/25.03 |
| 2015/0247828 A1* | 9/2015 | Ruellan | G01N 27/18 |
| | | | 73/23.4 |
| 2016/0018365 A1* | 1/2016 | Agah | B01J 20/223 |
| | | | 73/23.41 |
| 2016/0025694 A1 | 1/2016 | Brandau | 73/25.03 |

OTHER PUBLICATIONS

French Preliminary Search Report dated Apr. 15, 2016 in French Application 15 56724, filed on Jul. 16, 2015 ( with English Translation of Categories of Cited Documents).

S. Udina et al. "A micromachined thermoelectric sensor for natural gas analysis: Multivariate Calibration results", Sensors and Actuators B 166, 2012 11 pages.

Kurt Kliche et al "Sensor for Thermal Gas Analysis Based on Micromachined Silicon-Microwires", IEEE Sensors Journal, vol. 13, No. 7, 2013, 10 pages.

"7866 Digital Thermal Conductivity Analyzer for Binary Gas Mixtures", Honeywell, 70-82-03-46, Nov. 2005, 16 pages.

D. Cruz et al."Microfabricated thermal conductivity detector for the micro-ChemLab™", Science Direct, Sensors and Actuators B, 121, 2007, 9 pages.

* cited by examiner

DEVICE FOR ANALYSIS OF MIXTURES OF AT LEAST TWO GASES

TECHNICAL FIELD AND STATE OF THE PRIOR ART

The present invention relates to a gas sensor enabling the analysis of a mixture of at least two gases, in particular the measurement of the concentration of the gaseous components in a mixture of at least two gases.

The thermal conductivity of a gas mixture depends on its composition. Thus, depending on the concentration of each of the gases, the thermal conductivity of the mixture varies. This property is used to produce gas sensors. Measurement of the thermal conductivity makes it possible to relate back directly to the composition of a binary gas mixture of known nature.

In fact, considering a mixture of gases A1 and A2 and noting:

x1, x2 the respective molar fractions of gases A1, A2, and $\lambda(x_1, x_2, T_0, P_0)$ the thermal conductivity of the gas mixture with the molar fractions $x_1$, $x_2$, at temperature $T_0$ and at pressure $P_0$.

This gives:

$$\begin{cases} x_1 + x_2 = 1 \\ \lambda(x_1, x_2, T_0, P_0) = m1 \end{cases}$$

In fact the sum of all of the fractions of gases is equal to 1. For a fixed gas temperature and pressure, the thermal conductivity of the mixture then only depends on a parameter $x_1$.

Making the hypothesis that the thermal conductivity as a function of the composition of the mixture is known and monotonous, the measurement thereof then makes it possible to relate back to the molar fraction x1 and thus the composition of the mixture.

Nonetheless, this method is not applicable when there are more than two gases. If x1, . . . , xn denotes the respective molar fractions of gases A1, . . . , An, a single measurement does not make it possible to determine x1, . . . , xn and thus the composition of the mixture. It is in fact possible that two mixtures or more having different values x1, . . . , xn have the same thermal conductivity. It is then not possible to choose between the mixtures.

Yet the thermal conductivity depends on the temperature. It is thus possible by carrying out measurements at several temperatures of the gaseous mixture to obtain n equations, and thus n−1 measurements for determining x1, . . . , xn.

The document "*A micromachined thermoelectric sensor for natural gas analysis: Thermal model and experimental results*" Udina, S., Carmona, M., Caries, G., Santander, J., Fonseca, L., Marco, S. (2008) *Sensors and Actuators, B: Chemical*, 134 (2), pp. 551-558 describes a sensor making it possible to measure the concentration of several gases. This sensor implements a membrane suspended from a silicon substrate and a polysilicon heating means arranged on the membrane. The membrane is arranged in a chamber containing a gas mixture. An electric voltage is applied to the terminals of the heating means in order that it heats the membrane. Thermal exchanges take place with the gas mixture. A thermopile measures the temperature of the membrane, said temperature varying as a function of the composition of the gaseous mixture. Different electrical voltages are applied to the heating means to carry out several measurements at different temperatures.

The determination of the composition of the gaseous mixture is relatively long because it requires carrying out successively as many measurements at different temperatures as gases contained in the mixture, all the more so in that it is indicated that around 15 minutes are required before each measurement to ensure there is a stationary concentration in the chamber.

The document U.S. Pat. No. 4,164,862 also describes a device for measuring the composition of a mixture of n gases. This comprises N measurement chambers supplied in parallel by the gas mixture, each chamber being at a different temperature. To measure the thermal conductivity, each chamber comprises an electrical resistance forming part of a bridge, which is subjected to the flow of gas. The variation in the value of the resistance varies as a function of the temperature, which varies as a function of the gas composition. The resistance is supplied with current which, by Joule effect, releases heat. Due to the flow of the gas, the temperature of the resistance decreases, this decrease being a function of the thermal conductivity of the gas and thus of its composition. A feedback loop is provided to modify the intensity of the current flowing in the resistance and does so as a function of the temperature of the resistance. The feedback command is thus proportional to the thermal conductivity of the gas mixture.

This device is relatively bulky since as many chambers are required as compounds in the gaseous mixture.

DESCRIPTION OF THE INVENTION

It is consequently an aim of the present invention to offer an analysis device that can analyse a gaseous mixture comprising at least two gases offering a rapid analysis and a reduced size.

The aforementioned aim is attained by a device for analysing a mixture of n gases, comprising a microfluidic channel in which is intended to flow the gaseous mixture to analyse, at least n−1 suspended elements in the channel such that the n−1 suspended elements are at different positions in the channel. The device also comprises heating means so as to heat each volume of gaseous mixture that surrounds each suspended element to a given temperature different to those of the other volumes of gaseous mixture, and means of measuring the temperature of each suspended element or of a parameter dependent on the thermal conductivity of the gaseous mixture.

The inventors have noted that it is possible, using suspended micrometric elements in a microfluidic channel, on the one hand to rapidly thermalize individually to a given temperature a volume of the gas mixture surrounding each suspended element and, then, to measure the thermal exchanges between each suspended element and the volume of gas thermalized to the given temperature. Thus the inventors obtain simultaneously measurements at different temperatures. The analysis is then rapid and the device has a reduced size. Moreover, since the volumes of gas to thermalize are very small, the device necessitates low power for its operation.

On account of the small size of the channel, the filling of the channel and the homogenization of the gaseous mixture in the channel are rapid.

In other words, a gaseous environment at a given temperature is created at the scale of a suspended element and the thermal exchanges between the suspended element and the gaseous environment at this given temperature are measured, which makes it possible to determine, in an embodiment, the thermal conductivity of the gaseous mixture at this temperature. By using several suspended elements in a gaseous environment at different temperatures, the thermal conductivities of the same mixture are determined but at different temperatures, which makes it possible to relate back to the concentrations of each constituent of the gaseous mixture, these constituents being known. The measurement of the thermal conductivity at a given temperature may be carried out with known means, for example each suspended element may form part of a TCD (Thermal Conductivity Detector).

In an embodiment, each volume of gas comprises a suspended element. The size of the suspended elements and their arrangement with respect to each other are such that they ensure that they have no or little thermal influence on each other. In an embodiment example, the elements are formed by suspended membranes of micrometric dimensions, and at least one electrical conductor on one face of the membrane forms both the means of heating the gaseous mixture and the means of measuring the temperature of the membrane, for example by measuring the variation in electrical resistance of the electrical conductor which depends on the temperature. In another embodiment example, the elements are formed by wires of micrometric dimensions stretched transversally in the channel and forming directly the means of heating by Joule effect and of measuring the temperature. In a variant, the heating means may be a suspended wire at a distance from the suspended element.

In another embodiment, heating means common to the different suspended elements that form the measuring means are used.

The measurement of the variation in the electrical resistances of the electrical conductor or the suspended wire makes it possible to relate back to the composition of the gaseous mixture.

In a variant or in an additional manner, it is possible to measure the thermal conductance and/or the thermal capacity and/or any other physical parameter dependent on the thermal conductance and/or the thermal capacity, for example a temperature, a resistance, a voltage, a current.

The subject matter of the present invention is then a device for analysing a mixture of at the most n gases, comprising a microfluidic channel extending between a first end and a second end, at least n–1 suspended elements in the microfluidic channel, said n–1 elements succeeding each other from the first end of the microfluidic channel to the second end of the microfluidic channel, heating means capable of heating a zone of the gaseous mixture surrounding each suspended element to a given temperature different to those to which are heated the gaseous mixtures surrounding the other suspended elements, means of measuring the temperature or the variation in temperature of each suspended element and a control and measurement system connected to the heating means and to the measuring means.

Preferably, the conduit has a rectangular transversal section having a height and a width and wherein the distance between the heating means and the measuring means is less than the height of the channel.

The subject matter of the present invention is also a method of analysing a gaseous mixture of n gases, including the steps:

a) Introducing the gaseous mixture comprising n known components into a fluidic channel, the fluidic channel comprising at least n–1 suspended elements in the channel, said suspended elements being arranged one beside another in a direction of flow of the gaseous mixture in the microfluidic channel, b) Heating a volume of gas surrounding each suspended element to a given temperature different to those of the other volumes of gas, c) Measuring a parameter linked to the thermal exchanges with the gaseous mixture at each given temperature, d) Determining a concentration xj of each component of the gas mixture from the n–1 measurements obtained at step c).

BRIEF DESCRIPTION OF THE DRAWINGS

The present invention will be better understood on the basis of the description that follows and the appended drawings in which.

DETAILED DESCRIPTION OF PARTICULAR EMBODIMENTS

Figure 1:
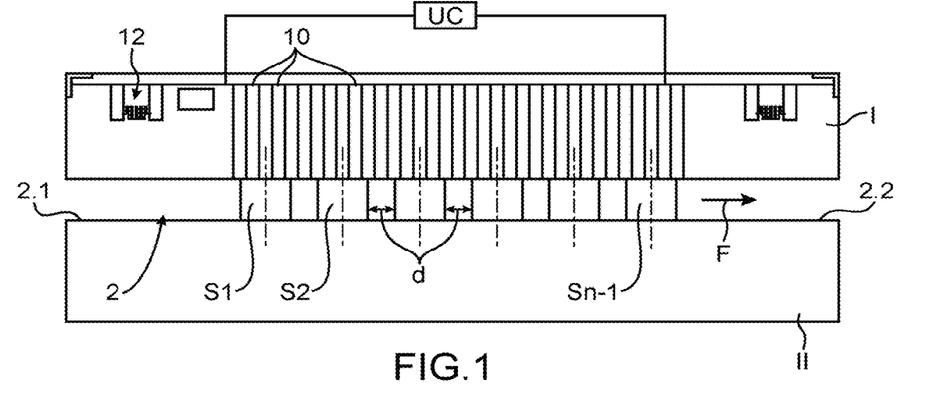
FIG. 1 is a longitudinal sectional view represented schematically of an example of device for analysing a gaseous mixture according to a first embodiment.

In FIG. 1 may be seen a schematic representation of a first embodiment of a device for analysing a gaseous mixture according to the invention. The gaseous mixture comprises n gases, n being a positive integer >1. The sectional plane is horizontal.

The device comprises a microfluidic channel 2 comprising a supply end 2.1 intended to be connected to a supply of gaseous mixture to analyse and an evacuation end 2.2. The gaseous mixture to analyse is thus intended to flow in the channel in the direction symbolized by the arrow F, at least during filling. The channel is for example made in two parts, for example by etching of two substrates made of semiconductor material, for example made of silicon or a substrate made of semiconductor and a glass substrate. The channel has in this example a rectangular transversal section.

As will be seen later, the analysis may then take place while the gaseous mixture is immobile, in this case it is possible to provide that the channel only comprises one open end through which take place the supply and the evacuation of gaseous mixture.

In a further variant, the channel may comprise more than two openings. For example, the device may comprise a porous cover or a cover provided with several holes, the cover enabling the pump-free exchange with gas outside the cavity, for example in mobile telephony type applications in which the implementation of a pump cannot be envisaged.

In the example represented, the channel 2 is straight and extends along a longitudinal axis X. It will be understood that the channel can have any profile, for example curved or in a spiral.

The device also comprises at least n−1 suspended elements S1, S2 . . . Sn−1 in the channel 2, the number of suspended elements being at least equal to 2. The device is capable of analysing the gaseous mixture comprising n different gases.

The elements are arranged at different places along the direction of flow F, i.e. the elements S1, S2 . . . Sn−1 are arranged one after the other at a distance from each other so as to each occupy a section of the channel 2. In the example represented, the suspended elements are separated by a constant distance d. In a variant, this distance could vary between two suspended elements and the following. In the case of a straight channel, the suspended elements each have a given emplacement along the longitudinal axis.

Figure 2:
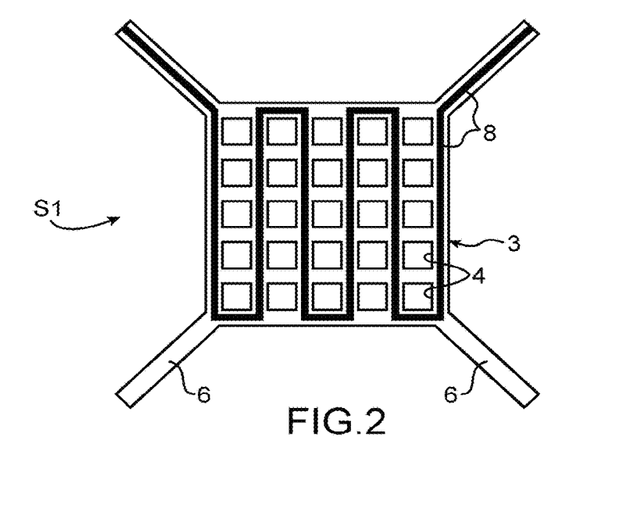
FIG. 2 is a top view represented schematically of an example of a suspended element in the microfluidic channel.

In FIG. 2 may be seen an example of an element S1 that can be suspended in the channel 2. It is a membrane 3 of square or rectangular shape and advantageously pierced by holes 4. The membrane 3 is suspended in the channel at the level of its four corners by arms 6. The holes 4 have the advantage on the one hand of aiding the release of the membrane during the different production methods and on the other hand of reducing the thermal capacity of the membrane. Advantageously, the arms all have the same length. Preferably, the arms have a small section and/or a long length in order to limit thermal leakages from the membrane to the substrate. A solid membrane and/or of different shape and/or suspended by two or three arms or more than four arms does not go beyond the scope of the present invention.

Preferably, the membrane is arranged parallel to the flat base of the channel.

The device comprises means of heating the volume of the gaseous mixture surrounding each suspended element S1, S2 . . . Sn−1 to temperatures T1, T2, . . . Tn−1 different to each other.

The device also comprises means M of measuring the thermal exchanges between the suspended element Si and the volume of gas at the temperature Ti, $1 \leq i \leq n-1$. The measurement of these thermal exchanges makes it possible to relate back to the thermal conductivity of the gaseous mixture at the temperature Ti or to any parameter dependent on the thermal conductivity.

In FIG. 2, the heating means are formed by a thermoresistive electrical conductor 8 formed on one of the faces of the membrane. It extends between two suspension arms 6 and advances along the membrane so as to occupy the surface of one of the faces in a substantially uniform manner. In the example represented, the conductor 8 is slot-shaped.

The means of measuring the temperature or the variation in temperature use the electrical conductor making it possible to measure the thermal exchanges between the suspended element and the gaseous mixture, which are representative of the thermal conductivity of the gaseous mixture at the given temperature.

The electrical conductor is connected to voltage or current electrical supply means and to current or voltage measuring means respectively.

The measuring means measure for example a voltage at the terminals of the electrical conductor or the current flowing in the electrical conductor.

In an example of operation, the heating means apply a direct voltage and the measuring means measure a current that is representative of the temperature of the membrane and thus the thermal exchanges between the membrane and the gaseous environment.

In another example of operation, the heating means apply to the conducting wire a direct voltage to heat the volume of gas Vi to Ti and the measuring means apply an alternating signal to the conducting wire making it possible to measure the thermal conductivity by applying temperature excursions to the membrane and by measuring the thermal exchanges between the membrane and the volume of gas.

Each conductor element is connected individually to the electrical supply means and to the measuring means.

The conductor element 8 is directly in contact with the membrane, its resistance is going to depend directly on the temperature of the membrane. By measuring the variation in voltage due to the variation in the electrical resistance of the electrical conductor at Ti, it is possible to relate back to the variation in the temperature of the membrane which depends on the thermal conductivity of the gaseous mixture at Ti and thus on its composition.

In a variant, the device could comprise a plurality of chips each including a channel and a membrane suspended in the microfluidic channel 2. Moreover, each chip could comprise its heating means, for example a resistance situated on the rear face of the chip. The heating means could heat the chip and the gas contained in the channel. Each membrane could comprise for example a conductor on which could be imposed a direct voltage or alternating voltage or a weak direct or alternating current, to measure the thermal exchanges between the membranes and the gas. This variant has the advantage of uniformly heating the gaseous mixture contained in each channel.

Preferably, the analysis device is produced by microelectronic techniques and comes in the form of a chip of which the contact pads are connected to a control and measurement system UC (FIG. 1) comprising means of electrically supplying the electrical conductors. In FIG. 1 are shown schematically the contact pads 10 intended to connect the electrical conductors to the control and measurement system UC. In the example represented, they are formed for example by deposition on the lower substrate. But both the upper substrate and the lower substrate or the lower substrate uniquely could comprise contact pads.

In an advantageous manner, heating means are provided to heat the microfluidic channel to a given temperature, for example by deposition of metal conductor on one of the faces of the lower or upper substrate of the chip. The heating means are for example of Joule effect type.

Means of measuring the temperature 12 of the substrate in which is formed the channel are advantageously provided in order to know the temperature of the walls of the channel during measurements and in order to be able to take it into account during the processing of the measurements.

The implementation of a microfluidic channel, i.e. having a small section, enables the appearance of different sections of gas thermalized to temperatures while having available a compact device. In fact the small section of the channel makes it possible to localize the heating of gas only around each membrane.

Figure 4:
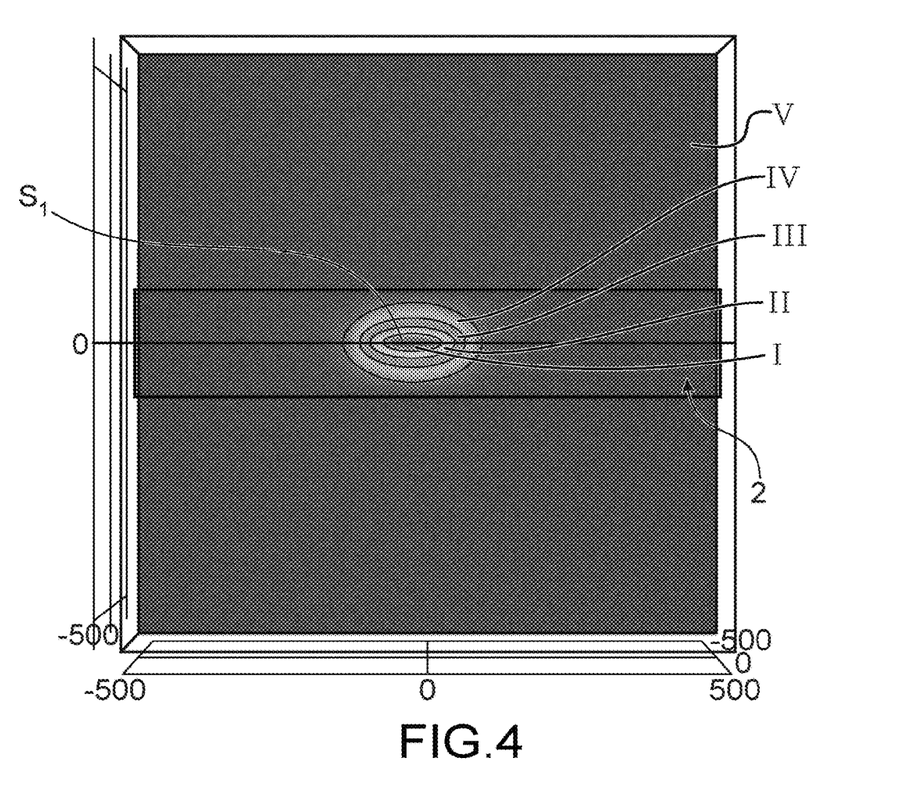
FIG. 4 is a representation of a suspended element and the volume of heated gas that surrounds it.

In FIG. 4 may be seen represented schematically a simulation of the heating of the volume of gas around a square membrane S1 of 150 μm sides suspended in a microfluidic channel of transversal section 200 μm×200 μm and 1000 μm length. The membrane is immersed in a gas, for example air, within the channel. A power of 0.125 W is used, for example obtained with a voltage of 5V arriving on a resistance of 200Ω. The external surfaces of the substrate in which is etched the channel are maintained at room temperature. The simulation shows that in the volume of gas localized around the membrane, typically in a zone extending between 50 μm above and 50 μm below, the temperature can reach temperatures above 500° C.

Zone I corresponds to a temperature above 800° C.

Zone II corresponds to a temperature between around 600° C. and 800° C.

Zone III corresponds to a temperature between around 400° C. and 600° C.

Zone IV corresponds to a temperature between around 200° C. and 400° C.

Zone V corresponds to a temperature less than 200° C.

This simulation thus shows that, in the device according to the invention, the temperature of the volume of gas around the suspended element can locally reach several hundreds of degrees using a power of the order of 0.1 W. In addition, it shows that the rise in temperature is located around the membrane, typically over a distance of 100 μm, and that by arranging the membranes at several hundreds of microns from one another, it may be considered that each membrane has its own thermal environment.

It is then possible to heat to different temperatures each volume of gas around each suspended element and thus to determine simultaneously the conductivity of the gaseous mixture at different temperatures or another parameter linked to the thermal exchanges and dependent on the composition of the gaseous mixture.

Preferably, in the case of a channel of transversal square section the distance between two facing edges of two membranes is of the order of a length of a side of the channel. For example, in the case of a channel of 200 μm×200 μm, the distance between two facing edges of two successive membranes is 200 μm.

The distance between two facing edges of two successive membranes is chosen notably as a function of the section of the channel. In fact it is observed that the distance over which the gas is heated around the membrane is around a half-height of the channel all around the channel. Typically, the distance between the two facing edges of two successive membranes is equal to around a height of the channel. For example in the case of a microfluidic channel of 200 μm×200 μm, the distance between the two facing edges of two successive membranes is of the order of 200 μm.

The microfluidic channel has for example a height and a width comprised between 50 μm and 1000 μm and a length comprised between 500 μm and 10000 μm. Preferably, the channel has a length and a width less than 500 μm, typically equal to 200 μm. This small section makes it possible to take practically instantaneously a volume of gas around the suspended element to a set temperature Ti and to minimize the consumption of the device. In addition, it also makes it possible to localize the heating of gas around the membrane over a distance of the order of 100 μm.

The membranes have for example a length and a width comprised between 2000 μm$^2$ and 200000 μm$^2$ For example for a rectangular membrane, it may have the length of a side comprised between 10 μm and 200 μm and the length of the other edge comprised between 200 μm and 1000 μm.

The suspension arms have for example a length of several tens of μm, for example between 10 μm and 100 μm and a width of several μm to several tens of μm, for example between 15 μm and 30 μm.

The membranes are advantageously made of SiN which has a thermal conductivity 60 times less than silicon. The electrical conductors may be made of any conducting material, for example platinum.

In the first embodiment, the suspended elements are preferably suspended membranes. Nevertheless, in a variant, the membranes could be replaced by conducting wires.

In a further variant, each volume of gas could comprise a heating element advantageously formed by a conducting wire and a measuring element, advantageously formed by a conducting wire.

The operation of the analysis device will now be described.

The gaseous mixture comprising at the most n known gases is introduced into the channel at the supply inlet 2.1.

In an operating mode, the evacuation outlet 2.2 is sealed off and the gaseous mixture is static in the channel during the measurements.

In another operating mode, the gas flows in the channel between the inlet 2.1 and the outlet 2.2 during the measurements but the flow is such that it does not create turbulences at the level of the suspended elements.

In another operating mode, the inlets of the cover or channel are open and the gas enters into the chip by diffusion or convection.

According to an advantageous example of operation, the control and measurement system individually supplies the electrical conductors with a direct voltage so as to heat the volume of gaseous mixture Vi to a working temperature Ti. Given the small volume of gas considered, this working temperature is reached very rapidly, typically in a time less than 1 ms for each volume Vi. The control and measurement system also supplies the electrical conductors with an alternating signal so as to impose a temperature excursion on the suspended element Si around the working temperature Ti. The membranes being surrounded by the gaseous mixture at Ti, they exchange heat with the gaseous mixture.

The control and measurement system measures the intensity at the terminals of the electrical conductor to know its thermoresistance and to deduce therefrom the temperature of the suspended element. Knowledge of this temperature makes it possible to determine the thermal conductivity λi(Ti).

The temperature may rise from one suspended element to the other in a monotonous manner or the temperatures of the suspended elements may be spread out randomly.

As shown above, the suspended elements being sufficiently small and being sufficiently far apart from each other, the heating delivered by the electrical conductor of one of the suspended elements does not influence or influences very little the temperature of the neighbouring gas zones and neighbouring suspended elements. It is then possible to carry out simultaneously measurements on all the suspended elements and at different temperatures.

The Wassiljewa equation below may then be used, which makes it possible to approximate the thermal conductivity of a gas mixture $$\lambda m = \sum_{i=1}^{n} \frac{xi\lambda i}{\sum_{j=1}^{n} xiAij}$$

With λm the thermal conductivity of the mixture,
λi the thermal conductivity of the component i, xi the concentration of the compound i, and Aij a function that is for example given in the document *A micromachined thermoelectric sensor for natural gas analysis: Thermal model and experimental results*" Udina, S., Carmona, M., Caries, G., Santander, J., Fonseca, L., Marco, S. (2008) *Sensors and Actuators, 8: Chemical*, 134 (2), pp. 551-558

Each suspended element operating around T1, . . . , Tn−1 then makes it possible to determine the thermal conductivity of the gaseous mixture at each temperature T1, . . . , Tn−1, i.e. λm(T1), . . . λm(Tn). Knowing moreover the values of the thermal conductivity of each of the n gases of the gaseous mixture at the temperatures T1, . . . , Tn−1, it is possible to resolve the system of n equations with n unknowns:

$$\begin{cases} x_1 + \ldots + x_n = 1 \\ \lambda(x_1, \ldots, x_n, T_1, P_0) = m_1 \\ \ldots \\ \lambda(x_1, \ldots, x_n, T_{n-1}, P_0) = m_{n-1} \end{cases}$$

The fractions $x_1 \ldots x_n$ are then obtained.

In an alternative manner to the use of the Wassiljewa equation, it is possible to relate back to the composition of the gaseous mixture from the measurements carried out after having conducted a first calibration step. This calibration step consists, on a test bed making it possible to mix the gases in a calibrated manner, in measuring the responses of the n−1 suspended elements (of voltage, current or thermal conductivity type) on several points of the composition domain of the mixture of interest. By data processing methods (for example by interpolation), it is then possible to estimate the responses of the n−1 elements between the points used for the calibration.

The operation of an analysis device wherein the suspended elements are suspended wires is similar to that described above. The heating wire serves both to heat the volume of gas surrounding it and for the measurements. In the case where each volume has a heating element and a measuring element, the signal supplied by the measuring element provides information on the thermal conductivity of the gaseous mixture between the heating element and the measuring element.

Figure 3:
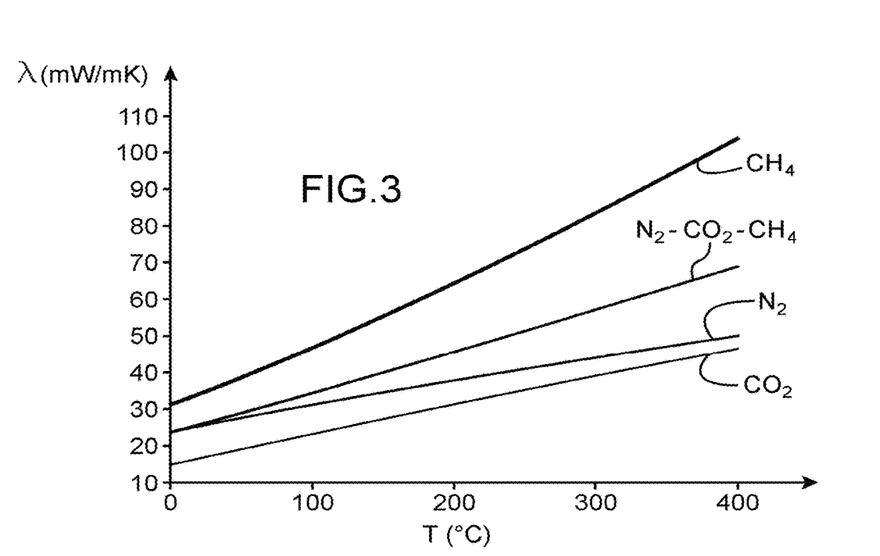
FIG. 3 is a graphic representation of the variation in the thermal conductivity in mW/mK of a gaseous mixture as a function of temperature.

In FIG. 3 may be seen a graphic representation of the variation in the thermal conductivity Δ in mW/mK of $N_2$, $CO_2$, methane and a mixture of $N_2$, $CO_2$ and methane as a function of the temperature T in ° C. These variations in conductivities are known.

It may be noted that a measurement at 20° C. does not make it possible to distinguish $N_2$ and the mixture.

Thanks to the device according to the invention, from the measurements of thermal conductivities of the gaseous mixture and knowledge of the thermal conductivities of the compounds of the mixture at the temperatures imposed in each section of the channel, it is possible to distinguish $N_2$ from the mixture and to do so in a rapid manner.

According to an advantageous variant, it may be envisaged that each suspended element is mounted in a Wheatstone bridge with an element arranged outside of the channel. Such a mounting makes it possible to eliminate the influence of the variation in the external temperature on the measurements.

In a variant, it could be envisaged to implement two suspended elements in the same section of gas, the two elements being mounted in a Wheatstone bridge.

Figure 6:
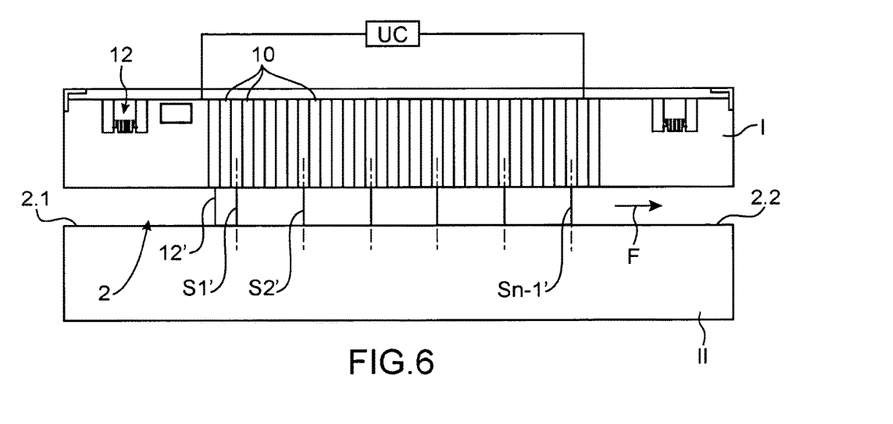
FIG. 6 is a schematic representation of an example of an analysis device according to a second embodiment.

According to another embodiment, heating means common to all the suspended elements are implemented, as is shown schematically in FIG. 6.

In an embodiment example, the heating means 12' comprise a conducting wire producing heat by Joule effect arranged at one end of the channel, the suspended elements S1', S2' . . . Sn.1', advantageously conducting wires are spread out in the channel. Each suspended element then is itself heated to a given temperature as a function of the thermal power dissipated by the heating wire and its emplacement with respect to the heating wire. This given temperature is for example determined during the calibration of the device. In this way sections of gas at given temperatures are defined.

In another example, the heating means impose a given gradient to the suspended elements. For example the heating means comprise a heating wire at one end of the channel and a heating wire at the other end of the channel, the suspended elements being suspended between the two heating wires. By supplying the two heating wires with current, a thermal gradient is imposed between the two heating wires. Each suspended element is then at a given temperature as a function of its emplacement between the two heating wires. In this way sections of gas at given temperatures are defined.

In this second embodiment, the suspended elements are preferably conducting wires.

The wires are suspended transversally in the channel. The wires are preferably parallel to a longitudinal section plane of the channel.

The suspended wires have for example a width and thickness comprised between 1 μm and 20 μm and a length comprised between 100 μm-1000 μm, i.e. the width of the channel.

The operation of the embodiment will now be described in the case of heating means with two heating wires.

The two heating wires are supplied electrically for example continuously so as to create a thermal gradient between them. Each section of gas surrounding each suspended element is at a given temperature. By applying a voltage to the terminals of each suspended element, it is possible to measure the intensity which depends on its electrical resistance and thus on the temperature. Yet the temperature depends on the composition of the gaseous mixture at the given temperature surrounding the suspended element. By measuring the intensity at the terminals of the suspended elements in the different sections of gas at different temperatures, it is possible to relate back to the composition of the gaseous mixture.

In a variant, the heating means could be supplied with alternating voltage.

An analogy may be made between this measurement example and the four points measurement technique of an electrical resistance with: the temperature which would be analogous to the electrical voltage, the heat flow which would be analogous to the current, the thermal resistance which would be analogous to the electrical resistance, the thermal capacity which would be analogous to the electrical capacity, the thermal conductor formed by the gas microchannel and the substrate which would be analogous to the electrical conductor, the temperature probe would be analogous to the voltmeter and the thermal source would be analogous to the current source.

In this embodiment, the measurement wires are under the thermal influence of the heating wire(s). Preferably, the measurement wires are located at a distance from the heating wire(s) less than or equal to the length of a side of the channel, for example they are located at more than 200 µm from the heating wire for a channel of 200 µm×200 µm.

In the above examples, the parameter of the gas mixture and of each of the gases considered to analyse them is the thermal conductivity. But other physical parameters capable of characterizing a gas or a gas mixture may be used such as the density, viscosity, sound speed, etc.

Uniquely as an example, an example of dimensioning an analysis device according to the invention is given.

Thermal conductivity detectors or TCD have typically a detection and precision limit of the order of 1 ppm, using the contrast of thermal conductivity with a vector gas with "high thermal conductivity" such as helium for example 152.0 mW·m$^{-1}$·K$^{-1}$). In the case of the analysis device according to the invention, the detection and precision limit can reach 1 ppm. The ratios of the thermal conductivities composing the gases to analyse could however be 10 to 100 times less than those obtained with helium, degrading the detection limit by as much. In fact, for a mixture of two gases A and B of different thermal conductivity, the variation in the signal over the full measuring range is in a first approximation greater when the difference in the thermal conductivities between A and B is larger. At equal noise level on the measurement, the concentration detection limits will thus be less good when the difference (and thus the full measuring range) between the thermal conductivities diminishes.

The analysis device may comprise electrical conductors having a resistance of the order of 100 Ohms. Under a voltage of 5V, they make it possible to thermalize locally the gas to temperatures greater than 500° C. The power dissipated in such a membrane remains however low 5×5/100 W=0.25 W. The power necessary for the sensor and the microcontroller will thus be several Watts, power that is for example compatible with a supply via a USB port which delivers a power between 5 W and 10 W.

The internal volume may be 100 µm×100 µm×10000 µm, i.e. 0.1 µL.

A flow rate of 1 mL/min makes it possible to fill the analysis cavity in a time less than 1 ms. The low thermal capacity of the membranes and the surround ing gas enables a rapid thermalisation in times of the order of or less than 1 ms. These response times of the sensor enable analyses in a time less than 10 s.

Such a device has an estimated cost less than 100€, a mass less than 500 g and an external volume of the order of 5 cm$^2$.

The analysis device according to the invention may thus have a reduced size, a limited cost price, a very short analysis time and a reduced electrical consumption.

In a very advantageous manner, the analysis device can advantageously replace gas phase chromatography column analysis systems or binary mixture gas sensor systems or be associated with a chromatography column.

A calibration of a device according to the invention and measurement of the composition of an axis will now be described.

The gas mixture $CO_2$, He, $N_2$ is considered.

The device used comprises two suspended membranes per section of gas at given temperature, the measurements on the two membranes being averaged.

The input voltage applied to the membrane is noted E. The output voltage linked to the measurement of the resistance or the current flowing through the thermoresistive wire of the membrane is noted V. It is for example a mounting of type: voltage measurement at the terminal of a resistance in series with the studied membrane; or a Wheatstone bridge type mounting. In order to sound the gas at different temperatures, different input voltages are applied to the membranes. In the example represented, the values of input voltage are applied: 3.5V, 5V, 6.5V, 8V.

Figure 7:
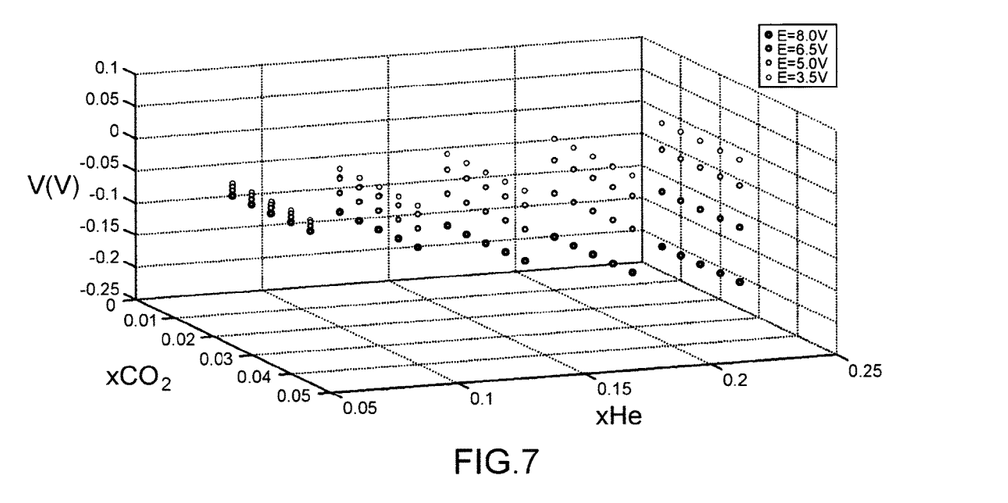
FIG. 7 is a representation of the experimental data of calibration of a device according to the invention with a mixture of $CO_2$, He, $N_2$.

The device is firstly calibrated over a defined composition domain. To do so, the device is placed at the outlet of a gas test bench which makes it possible to prepare the different compositions of the mixture $CO_2$, He, $N_2$. For each of these compositions, the output voltages of the different membranes are measured. All of the experimental results of calibration for $CO_2$ and He is represented in FIG. 7. The fraction of N2 is obtained by making $1-x_{CO2}-x_{He}$.

Figure 8:
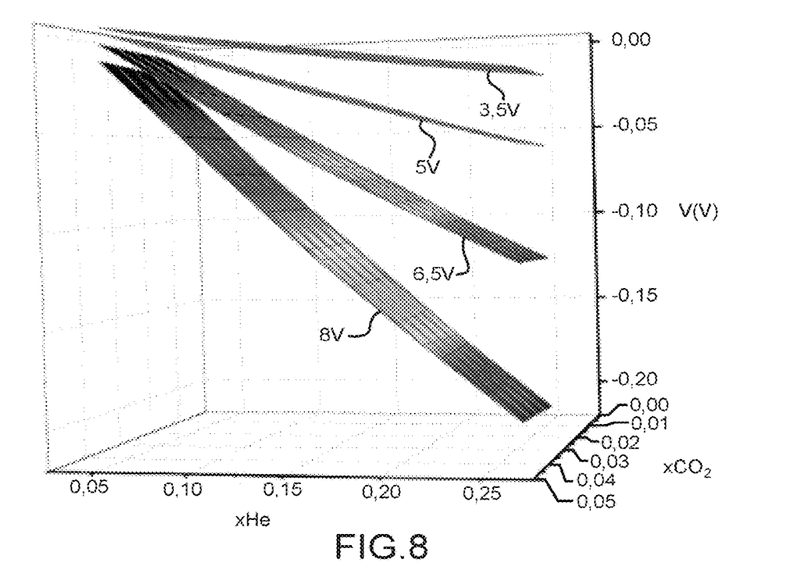
FIG. 8 is a graphic representation of a $2^{nd}$ order interpolation of the data of FIG. 8.

These experimental results are then 2$^{nd}$ order interpolated over the calibration domain. This interpolation ends up in the definition of the four surfaces represented in FIG. 8 and defined by the four equations for each of the input voltages.

$$(x_{CO2},x_{He}) \rightarrow V_{E=3.5V}(x_{CO2},x_{He})$$

$$(x_{CO2},x_{He}) \rightarrow V_{E=5V}(x_{CO2},x_{He})$$

$$(x_{CO2},x_{He}) \rightarrow V_{E=6.5V}(x_{CO2},x_{He})$$

$$(x_{CO2},x_{He}) \rightarrow V_{E=8V}(x_{CO2},x_{He})$$

The device having been calibrated and having available graphic representations linking the output voltage to the fractions of gas as a function of different input voltages, a gaseous mixture comprising $CO_2$, He, $N_2$ of known composition is analysed in order to check the performances of the device. The concentration of each of the gases is noted $x_{CO2}$, $x_{He}$, $x_{N2}$. The composition of the gaseous mixture is 3.5% $CO_2$, 15% helium, and 81.5% nitrogen.

The gas mixture is introduced into the microfluidic channel of the device. This gives experimental measurements of the output voltages for each of the input voltages. From the graphic representation of FIG. 8, it is possible to plot four straight lines represented in FIG. 9.

Figure 9:
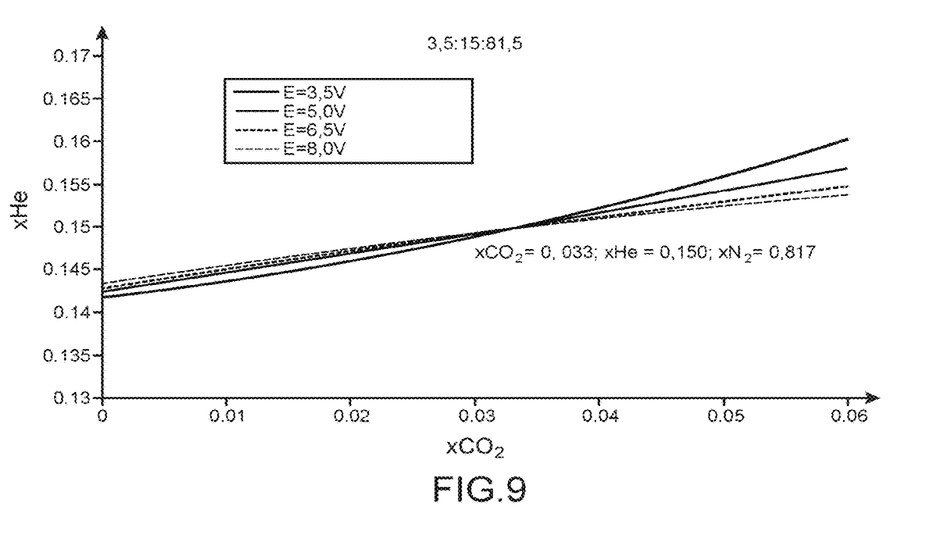
FIG. 9 is an experimental measurement carried out with a device according to the invention on a mixture of 5% $CO_2$, 15% helium, and 81.5% nitrogen.

It is shown here graphically how to proceed to relate back to an estimation of the composition of the ternary gas from these data of the sensor and calibration surfaces.

To determine $x_{CO2}$ and $x_{He}$, only two equations are necessary: the couple $x_{CO2}$ and $x_{He}$ then being defined at the intersection of the corresponding two curves. $x_{CO2}$ and $x_{He}$ then being determined, it is possible to determine $x_{N2}$ because $x_{CO2}+x_{He}+x_{N2}=1$.

It may be observed here, with the two additional measurements, that the curves intersect at a point close to $x_{CO2}=3.3\%$, $x_{He}=15\%$, $x_{N2}=81.7\%$.

A composition measurement error less than 1% is observed with respect to the composition of the mixture. The device according to the invention thus makes it possible to realize in a single operation the composition of a gaseous mixture comprising three compounds in an efficient manner.

An example of production method will now be described in relation with FIGS. 5A to 5K.

Figure 5A:
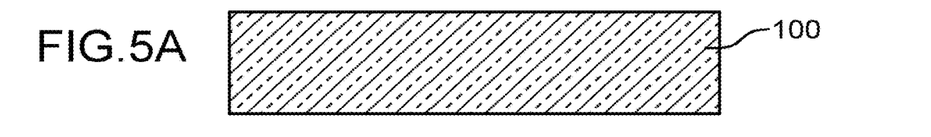
FIGS. 5A to 5K are schematic representations of steps of an example of method of producing an analysis device according to the invention.

The starting point is for example a substrate 100 made of semiconductor material for example made of Si having for example a thickness of 540 µm.

This is represented in FIG. 5A.

Figure 5B:
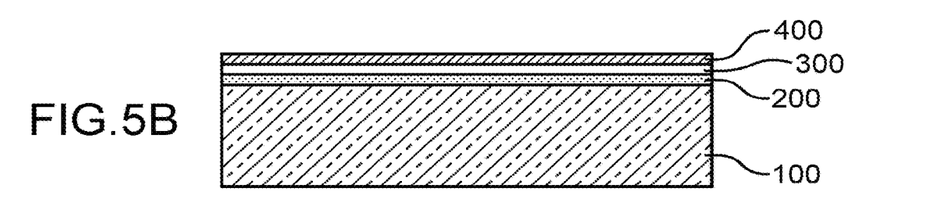

An oxide layer 200 is then formed, for example $SiO_2$ for example of 50 nm thickness, for example by thermal oxidation, then a layer of SiN 300 for example of 200 nm thickness for example by chemical vapour deposition, and a layer of an electrical conductor material 400 for example Pt, for example by sputtering, of 100 nm thickness.

The element thereby obtained is represented in FIG. 5B.

Figure 5C:
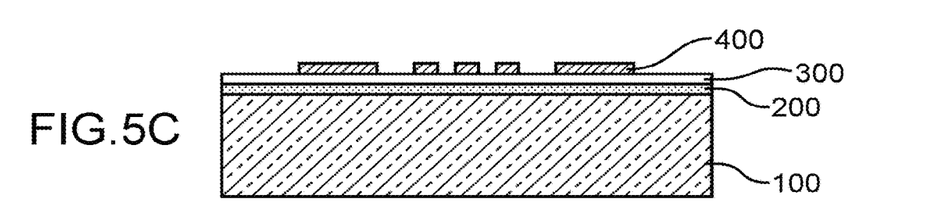

During a following step, the layer 400 is structured, for example by photolithography and ion etching. The resin remaining from the photolithography step is then removed.

The element thereby obtained is represented in FIG. 5C.

Figure 5D:
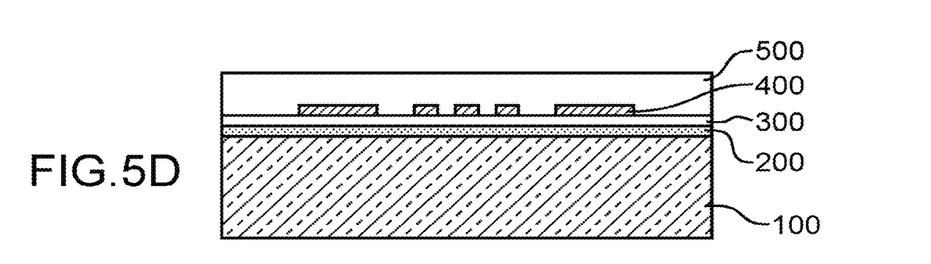

During a following step, an oxide layer 500 is formed on the structured layer 400, and having for example a thickness of 500 nm, for example by chemical vapour deposition.

The element thereby obtained is represented in FIG. 5D.

Figure 5E:
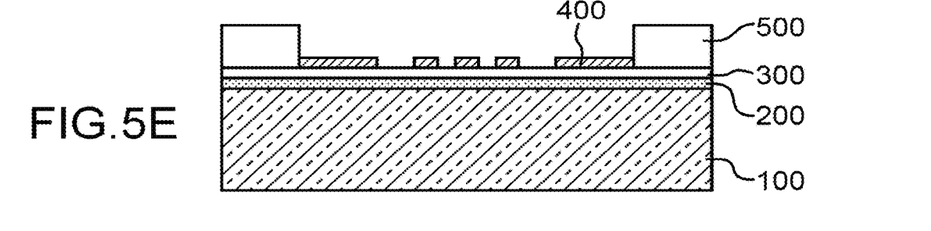

During a following step, the layer 500 is structured for example by photolithography, etching with stoppage on the layer 300 of SiN. The resin remaining from the photolithography step is then removed.

The element thereby obtained is represented in FIG. 5E.

Figure 5F:
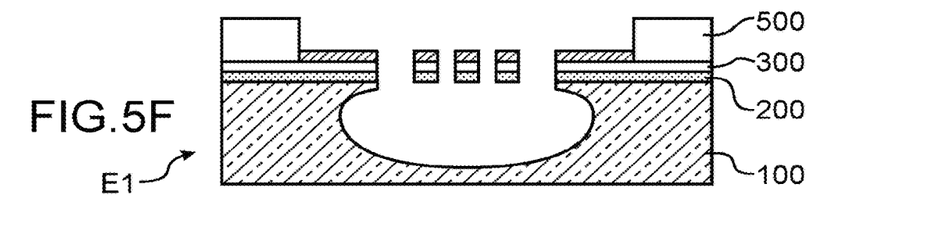

During a following step the substrate 100 is structured for example by photolithography, etching of the layers 300 and 200 for example anisotropic and isotropic dry etching. The resin remaining from the photolithography step is then removed The element thereby obtained, designated E1, is represented in FIG. 5F. It comprises suspended elements.

Figure 5G:
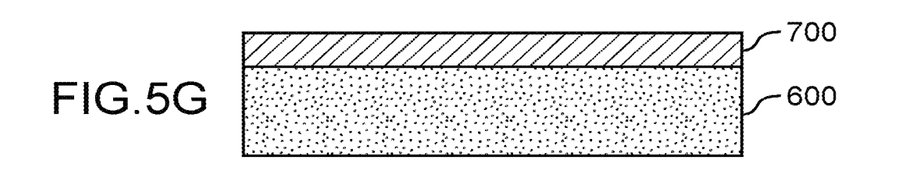

During a following step a cover E2 is produced. For example a glass substrate 600 is used on which a layer of W/WN/Au is formed, which will serve as mask, for example by deposition for example by sputtering, having for example a thickness of 200 nm.

The element thereby obtained is represented in FIG. 5G.

Figure 5H:
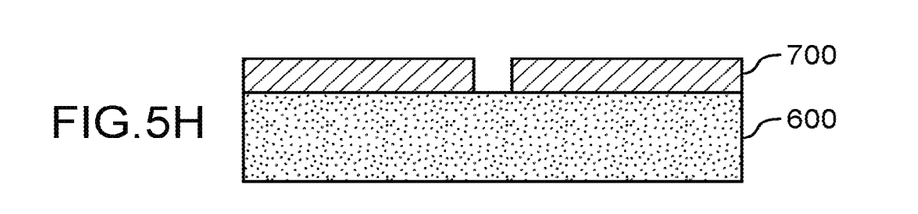

During a following step, the layer 600 is structured, for example by photolithography and etching of the layer 700 for example by wet HF etching. The resin remaining from the photolithography step is then removed.

The element thereby obtained is represented in FIG. 5H.

Figure 5I:
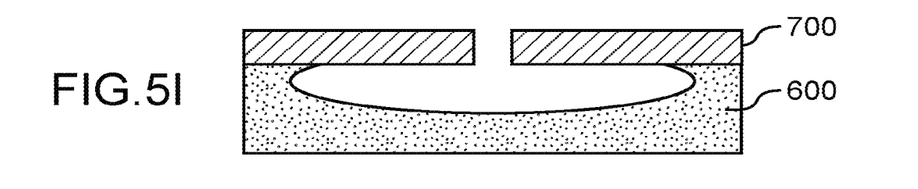

During a following step, an etching of the substrate 600 with HF is carried out.

The element thereby obtained is represented in FIG. 5I.

Figure 5J:
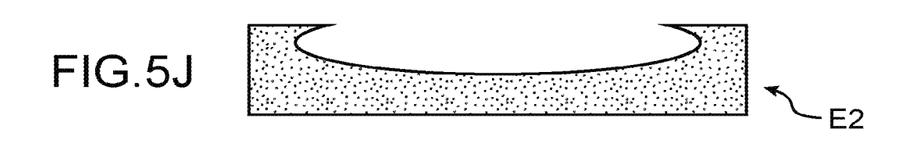

During a following step, the mask 700 is removed.

The element thereby obtained is represented in FIG. 5J. The element E2 is obtained, which is going to form a cover.

Figure 5K:
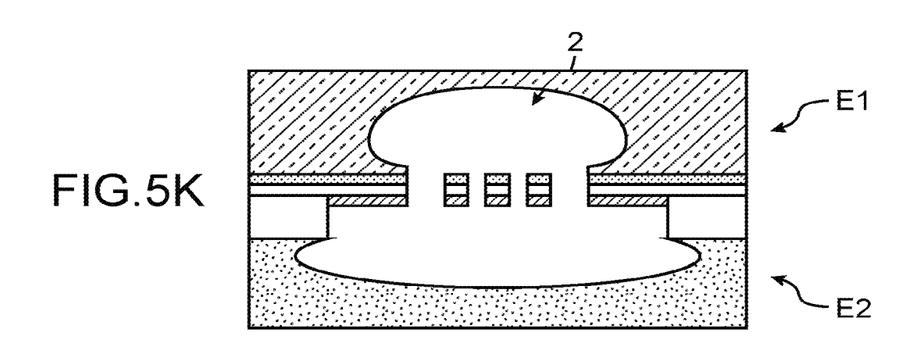

During a following step, the elements E1 and E2 are assembled, for example by anodic bonding. A microfluidic channel is thus delimited, in which are suspended the elements S1, S2, S3.

The element thereby obtained is represented in FIG. 5K.

The invention claimed is:

1. A device for determining the concentrations of n gases of a gaseous mixture, comprising:
   a microfluidic channel extending between a first end and a second end,
   at least n−1 suspended elements in the microfluidic channel, the number of suspended elements being at least equal to 2, said n−1 elements succeeding each other from the first end of the microfluidic channel to the second end of the microfluidic channel,
   at least one first electrical conductor configured to heat a zone of the gaseous mixture surrounding each suspended element, the at least one first electrical conductor and the arrangement of the suspended elements being such that each zone of the gaseous mixture is heated to a temperature different from temperatures to which the zones of gaseous mixture surrounding the other suspended elements are heated,
   at least one second electrical conductor configured to measure a temperature or a variation in temperature of each suspended element, and
   a control and measurement system connected to the at least one first electrical conductor and the at least one second electrical conductor, the control system commands the at least one first electrical conductor such that each zone of the gaseous mixture is heated to a different temperature, and determines thermal conductivity values at different temperatures of each zone based on the measured temperature or the measured variation in temperature for each suspended element to determine the concentrations of the n gases.

2. The device according to claim 1, wherein each volume of gaseous mixture comprises its individual electrical conductor.

3. The device according to claim 2, wherein the channel has a rectangular transversal section having a height and a width, the distance between two facing edges of two successive suspended elements is of the order of the height of the channel.

4. The device according to claim 2, wherein the distance between two facing edges of two successive suspended elements is comprised between 200 μm and 2000 μm.

5. The device according to claim 2, comprising n−1 chips each comprising a fluidic sub-channel arranged in the microfluidic channel of the device, the internal volume of the fluidic sub-channels being intended to contain a gaseous mixture zone, each suspended element being suspended in a fluidic sub-channel, the at least one first electrical conductor being situated on an external face of each chip.

6. The device according to claim 1, wherein each suspended element comprises a membrane suspended by suspension arms in the channel and wherein the at least one first electrical conductor comprises a conducting wire formed on one face of the membrane.

7. The device according to claim 6, wherein the membranes have surface areas comprised between 200 μm$^2$ and 200000 μm$^2$.

8. The device according to claim 6, wherein the suspension arms have a length on the order of tens of μm and a width between 15 μm and 30 μm.

9. The device according to claim 1, wherein each suspended element comprises at least one suspended wire.

10. The device according to claim 9, wherein the suspended wire forms the at least one first electrical conductor and the at least one second electrical conductor.

11. The device according to claim 1, wherein the at least one first electrical conductor is common to all volumes of the gaseous mixture.

12. The device according to claim 11, wherein the at least one first electrical conductor comprises at least one conducting wire intended to heat all volumes of the gaseous mixture.

13. The device according to claim 1, wherein the at least one first electrical conductor comprises plural electrical conductors arranged on either side of the suspended elements so as to impose a thermal gradient on the gaseous mixture situated between the electrical conductors.

14. The device according to claim 13, wherein the channel has a rectangular transversal section having a height and a width and wherein the distance between successive electrical conductors is less than or equal to the height of the channel.

15. The device according to claim 14, wherein the transversal section of the microfluidic channel is between 100 μm$^2$ and 1 mm$^2$.

16. The device according to claim 1, wherein the at least one first electrical conductor and the at least one second electrical conductor comprises electrical conducting wires suspended in the channel.

17. The device according to claim 16, wherein each suspended wire has a transversal section comprised between 1 μm and 20 μm and a length comprised between 100 μm and 1000 μm.

18. The device according to claim 1, wherein each suspended element is mounted in a Wheatstone bridge with at least one other suspended element arranged outside of the microfluidic channel.

19. The device according to claim 1, wherein the control and measurement system comprises an electrical supply configured to apply a continuous signal to heat the gaseous mixture and an alternating signal to measure the temperature or variation in temperature.

20. A method of analyzing a gaseous mixture of n gases, comprising:
  a) introducing the gaseous mixture comprising n known components into a microfluidic channel, the microfluidic channel comprising at least n−1 suspended elements in the channel, the number of suspended elements being at least equal to 2, said suspended elements being arranged next to each other in a direction of flow of the gaseous mixture in the microfluidic channel,
  b) heating a volume of gas surrounding each suspended element to a temperature different from temperatures of the other volumes of gas,
  c) measuring a parameter linked to thermal exchanges with the gaseous mixture at each temperature corresponding to each of the at least n−1 suspended elements to generate at least n−1 measured parameters,
  d) determining a concentration xj of each component of the gas mixture from the at least n−1 measured parameters.

21. The method of analyzing a gaseous mixture of n gases according to claim 20, wherein the heating takes place by heating the suspended element such that the volume of gas surrounding said suspended element is heated to a corresponding temperature.

22. The method of analyzing a gaseous mixture of n gases according to claim 21, wherein the introducing takes place by applying a direct voltage to an electrical conductor and wherein the heating takes place by applying an alternating voltage to the electrical conductor or to another electrical conductor.

* * * * *